United States Patent [19]

Joseph et al.

[11] Patent Number: 4,951,678
[45] Date of Patent: Aug. 28, 1990

[54] METHODS AND APPARATUS FOR MONITORING VITAL SIGNS

[75] Inventors: Jeffrey I. Joseph, Philadelphia; Daniel M. Benson, Springfield, both of Pa.

[73] Assignee: Thomas Jefferson University, Philadelphia, Pa.

[21] Appl. No.: 197,571

[22] Filed: May 23, 1988

[51] Int. Cl.$^5$ .............................................. A61B 5/08
[52] U.S. Cl. .................................... 128/671; 128/715; 128/773
[58] Field of Search ................ 128/671, 670, 715, 716, 128/773

[56] References Cited

U.S. PATENT DOCUMENTS

| | | | |
|---|---|---|---|
| 3,171,892 | 3/1965 | Pantle | 179/1 |
| 3,182,129 | 5/1965 | Clark | 179/1 |
| 3,210,747 | 10/1965 | Clynes | 128/670 |
| 3,348,535 | 10/1967 | Gregg | 128/715 |
| 4,141,350 | 2/1979 | Shinoda | 128/2.05 |
| 4,248,241 | 2/1981 | Tacchi | 128/671 |
| 4,304,240 | 12/1981 | Perlin | 128/671 |
| 4,484,583 | 11/1984 | Graham | 128/671 |
| 4,619,268 | 10/1986 | Uphold et al. | 128/671 |
| 4,672,977 | 6/1987 | Kroll | 128/773 |
| 4,686,998 | 8/1987 | Robbins | 128/670 |
| 4,704,029 | 11/1987 | Van Heuvelen | 356/39 |
| 4,705,048 | 11/1987 | Pfohl | 128/715 |

FOREIGN PATENT DOCUMENTS 158695 12/1978 Netherlands .

OTHER PUBLICATIONS

C. Perry, "We Do Need Precordial and Esophageal Stethoscopes", *Journal of Clinical Monitoring*, vol. 3, No. 3, p. 192 (Jul. 1987).

Webster, "Now That We Have Pulse Oximeters and Capnographs, We Don't Need Precordial and Esophageal Stethoscopes", *Journal of Clinical Monitoring*, vol. 3, No. 3, p. 192, (Jul. 1987).

Philip et al., "An Electronic Stethoscope is Judged Better Than Conventional Stethoscopes for Anesthesia Monitoring", *Journal of Clinical Monitoring*, 2(3):151-154, (Jul. 1986).

Waring et al., "Pulmonary Auscultation With the Littmann Differential (Double) Stetchoscope", (1979).

Wooten et al., "Method for Respiratory Sound Analysis" *Medical Instruments*, 12(4):254-267, (1978).

Huang et al., "Video Stethoscope-A Simple Method for Assuring Continuous Bilateral Lung Ventilation During Anesthesia", *Anesthesia and Analgesia*, 62:586-589, (1983).

(List continued on next page.)

Primary Examiner—Lee S. Cohen
Assistant Examiner—S. Getzow
Attorney, Agent, or Firm—Woodcock, Washburn, Kurtz, Mackiewicz & Norris

[57] ABSTRACT

Disclosed are methods and apparatus for the detection of inadvertent endobronchial intubation, esophageal intubation and other potentially dangerous complications arising from invasive monitoring, endotracheal intubation and mechanical ventilation during surgery. Methods of the present invention generally require producing a mixed electrial signal comprising the combination of a first electrical signal and a second electrical signal, the first electrical signal being representative of the sounds emanating from a first region of the patients body and the second electrical signal being representative of the sounds emanating from a second region of the patients body. The mixed electrical signal is converted into a display signal, and then the display signal is monitored while reducing the contribution of said first electrical signal in said mixed signal to a value substantially less than the contribution of said second signal in said mixed signal.

Apparatus comprising at least two electronic sound sensing devices are disclosed. Means for independently and adjustably amplifying the electrical signals are provided. The apparatus further includes means for mixing said amplified electrical signals to produce a mixed electrical signal. The output of the mixing means is connected to a signal transducer for converting said mixed electrical signal into a display signal.

18 Claims, 1 Drawing Sheet

OTHER PUBLICATIONS

Nelson, "A Monaural Stethoscope for Anesthesiologists", *Anesthesia and Analegesia*, 51:177–179, (1972).

P. 25 of a Medical Equipment Catalogue.

deLeon et al., "Group Teaching of Auscultation Uses of New Wireless Stethoscope Type Headphone", *American Journal of Cardiology*, 41:333–335, (Feb. 1978).

"Differential Auscultation with the Littman Differential Stethoscope", published by the Medical Products Division of 3M Corporation, 1979.

Douglass et al., "Esophageal Stethoscope Amplifier", *Anesthesia and Analgesia*, 64:377–378, (1985).

Abelson, "High Fidelity Electronic Stethoscope", *Journal of American Medical Association*, 218:741, (1971).

Catalogue pages disclosing different kinds of stethoscopes.

"Frequency Converters and Detectors", *Electronics Engineers' Handbook*, 2nd Edition, pp. 14–56 to 14–70.

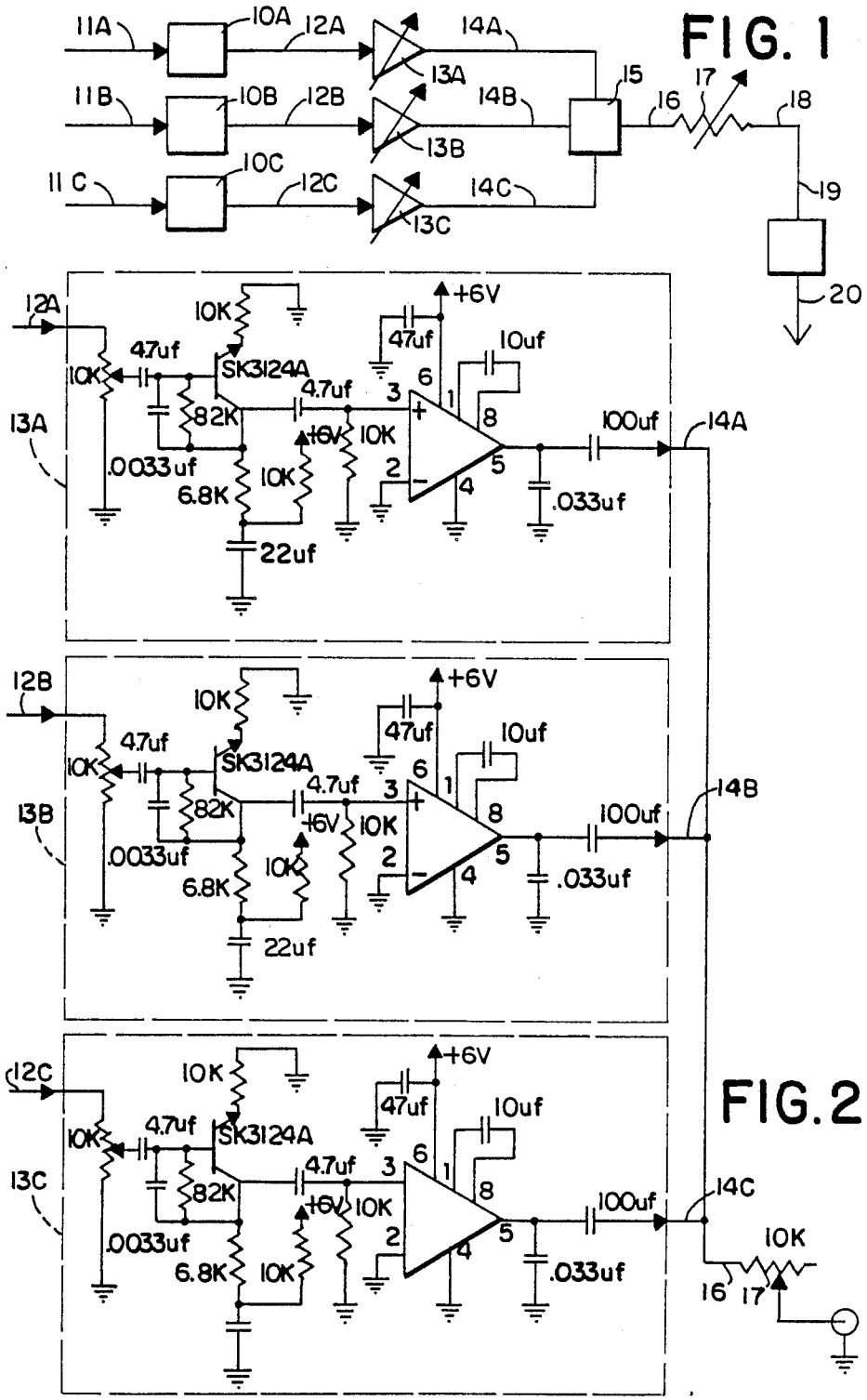

METHODS AND APPARATUS FOR MONITORING VITAL SIGNS

The present invention relates to methods and apparatus for monitoring the vital signs of a patient, and more particularly to methods and apparatus for detecting respiratory and cardiac abnormalities in anesthetized patients.

One major responsibility of the anesthesiologist in a surgical setting is to monitor the vital signs of the patient both before and during the operation. Modern techniques for monitoring the condition of a patient typically include pulse oximetry, electrocardiography and capnography. Although the potential benefit of traditional listening devices such as the precordial and esophageal stethoscopes is still recognized by some, the use of such traditional devices has been denounced by others as obsolete. See C. Perry, "We Do Need Precordial and Esophageal Stethoscopes", 192 *Journal of Clinical Monitoring* Vol. 3, No. 3 (July 1987) and T. A. Webster, "Now That We Have Pulse Oximeters and Capnographs, We Don't Need Precordial and Esophageal Stethoscopes" 192 *Journal of Clinical Monitoring* Vol. 3, No. 3 (July 1987). The denunciation of traditional monitoring devices has centered, at least in part, on the lack of detailed information these devices have heretofore been able to provide.

Anesthesiologists have traditionally used esophageal stethoscopes to monitor the heart and lung sounds of a patient under general anesthesia. A more modern version of such a device, as shown for example in U.S. Pat. No. 4,484,583—Graham, typically includes a plastic tube having a bore extending over the length of the tube. A microphone element is typically mounted in the distal end of the tube for detecting respiratory and heart sounds. The signals are conducted through wires arranged in the tube. One difficulty associated with esophageal stethoscopes of the type disclosed in Graham is that the single microphone does not provide the anesthesiologist with all the information necessary to properly monitor the condition of the patient. For example, the relatively high frequency lung sounds tend to obscure, at least to some extent, the low frequency heart sounds and vice versa. As a result, it is difficult for the anesthesiologist to diagnosis the condition of the patient based upon changes in heart and/or lung sounds. Other electronic esophageal stethoscopes are shown in U.S. Pat. No. 4,619,268—Uphold et al and in 4,304,240—Perlin. The patent to Perlin discloses an esophageal probe containing a first microphone at the distal end and a second microphone located a substantial distance proximally from the first microphone. In the inserted configuration, the first microphone is said to be located in a lower part of the esophagus in the proximity of the patient's heart, such that the first device receives predominantly heart sounds, although lung sounds will also be received in this position. The second microphone is located in an upper part of the esophagus to receive predominantly lung sounds. The gains of the signals from the two microphones may be adjusted, and the adjusted signal from the second microphone may be subtracted from the adjusted signal from the first microphone to remove the contribution of lung sounds detected by the first microphone. Thus, it is said that a signal representing pure heart sounds may be obtained. Despite these advances in esophageal stethoscopes, it is nevertheless not possible, due to the placement of the probe in the esophagus of the patient, to detect the relative strength and/or quality of lung sounds coming from distinct portions of the lung. It has been noted, for example, that pretracheal and esophageal stethoscopes are useless in indicating whether endobronchial intubation has taken place. See Webster at page 192.

A hybrid device which utilizes both an esophageal and a precordial stethoscope for monitoring the vital signs of a patient is disclosed in U.S. Pat. 4,705,048—Pfohl. The system includes a first sensor unit mounted on the patient's chest for picking up breath and heart sounds. A filter and an automatic gain control circuit is provided. The system also includes an esophageal stethoscope for monitoring a patient's vital signs during surgery. According to the system disclosed in Pfohl, only one signal can be monitored at any given time, thus limiting the amount of useful information available for the clinicians use. This system also has the disadvantage inherent with the use of esophageal stethoscopes as described above. Moreover, the use of a single precordial listening device makes it difficult for the anesthesiologist to perform bilateral auscultation of the chest during surgery. As noted by Webster at page 192, heretofore used precordial stethoscopes, especially in the surgical environment, are not practical and reliable tools for determining the occurrence of unilateral ventilation. As will be appreciated by those skilled in the art, the entire patient is often screened from the anesthesiologist during operating procedures by a multitude of surgical drapes. It is difficult, time consuming, unreliable and impractical for the anesthesiologist to crawl under the separating drapes during surgery to adjust the position of the precordial stethoscope. A similar problem attends to the patient monitoring apparatus shown in U.S. Pat. Nos. 4,248,241—Tacchi and 4,686,998—Robbins.

It has been said that the diagnosis of breathing circuit malfunctions requires that breath sounds be heard clearly, and that the anesthetist listen continuously and carefully to detect change or absence of breath sounds. These same requirements are said to apply equally to the detection of heart sounds. Electronic stethoscopes have been suggested as a means for addressing these goals. See for example Philip et al, "An Electronic Stethoscope is Judged Better Than Conventional Stethoscopes for Anesthesia Monitoring", 154 *Journal of Clinical Monitoring*, Vol. 2, No. 3 (July 1986). Also see U.S. Pat. No. 3,182,129—Clark et al.

Several patents and publications disclose apparatus adapted to permit the attending physician to simultaneously listen to and compare two different regions of the lungs. For example a report entitled "Pulmonary Auscultation with the Littmann Differential (Double) Stethoscope", Waring et al (1979) describes the use of a headset consisting of two sound transmission tubes and two chest pieces that are acoustically independent. It is said that sounds from the right chest piece are heard only in the right ear and that sounds from the left chest piece are heard only in the left ear. As a result, the user of such a device must develop the unusual and difficult skill of bilateral hearing in order to take advantage of the information provided thereby. Moreover, this device relies on audio tube transmission of the detected sounds and is accordingly subject to the sound quality and the mobility restriction disadvantages associated therewith.

U.S. Pat. No. 3,171,892—Pantle relates to an electronic apparatus adapted to receive input signals from a pair of individual pickup devices. It is said that the pickup devices may be of an acoustic nature such as microphones adhered to different parts of the body or simply electrodes meant to pickup electrical signals on the organism. The signals are amplified and then fed to a squaring stage which shapes the signals into square waves. Other filtering and signal exclusion is also carried out in the apparatus of Pantle. Thus, one object of the invention disclosed in the Pantle patent is to provide an apparatus which is able to discriminate and/or filter the signal coming from one of the microphones, thus allowing the observer to monitor only a portion of the signal coming from that single microphone. The apparatus of Pantle does not suggest or even allow the user to simultaneously monitor unaltered sounds originating from two distinct sources. In fact, the apparatus of Pantle is designed to avoid such an occurrence.

The report entitled "Method for Respiratory Sound Analysis", *Medical Instrumentation*, Volume 12, No. 4, Wooten et al (1978) describes the analysis of respiratory sounds by means of a dual channel sound envelope detector and a real time spectral analyzer. The apparatus includes a pair of microphones, each having a plastic annular ring placed thereover. The output of each microphone is fed into a separate amplifier system having a gain of about 250. The amplifier in turn feeds an active integrating network with an adjustable time constant so that the optimum sound envelope can be recorded. Both channels of the sound intensity analyzer are recorded on a multichannel tape recorder, a multichannel strip chart recorder or a storage oscilloscope. The integrating network disclosed in the Wooten article tends to alter the monitored sound by clipping the peaks of the audio signal and by transmitting only pieces of the signal occurring at certain points along the bandwidth. Thus, the Wooten apparatus does not produce a signal that is familiar to physicians accustomed to the sound produced by an ordinary stethoscope. Moreover, no means is provided for adjusting the gain on the amplifier coupled to each pickup device. Thus, the apparatus of Wooten does not allow the attending physician or clinician to monitor a single audio signal representative of the combined sounds sensed by each microphone, nor does it allow the amplifications of the individual signal to be adjusted with respect to one another.

The article by Huang et al, "Video Stethoscope-A Simple Method for Assuring Continuous Bilateral Lung Ventilation During Anesthesia", *Anesthesia and Analgesia*. Vol 62, No.586 (1983) describes a study in which two custom built electrically isolated microphones were attached to the left and right anterior or posterior chest wall of a patient. The signals from each microphone were separately amplified and filtered to eliminate cardiac and muscle artifacts. It is said that the filtered and amplified sounds were then played through an ordinary portable stereo system. There is no indication that the apparatus included means for mixing the electrical signals from each microphone. Moreover, there is no indication that the apparatus included means for adjusting the amplification of each electrical signal prior to those signals being mixed.

The ability of an anesthesiologist to detect, through auditory signals, the presence or absence of bilateral ventilation during surgical procedures can be a valuable asset. Applicants have found that the quality and nature of the lung sounds after endotracheal intubation can be a reliable indicator of the tube placement, provided the auditory signals are developed and manipulated as required by the present invention. Yet, heretofore used auscultation techniques have been largely ineffective or impractical for the accurate and/or reliable diagnosis of an inadvertent endobronchial intubation, even in the face of tremendous incentive and long felt need for such techniques. Blood diagnostic techniques have also proven to be less than completely satisfactory for the detection of endobronchial intubation. For example, arterial hemoglobin desaturation may not occur to a perceptible extent due to the sigmoid shape of the hemoglobin-oxygen dissociation curve, despite the progressive intrapulmonary shunting of blood that occurs after a mainstem intubation. Thus, since a moderate $FIO_2$ is often used in healthy anesthetized patients, pulse oximetry cannot be solely relied upon to detect a mainstem intubation. Accordingly, it is an object of the present invention to provide methods and apparatus for the detection of inadvertent endobronchial intubation, esophageal intubation and other potentially dangerous complications arising from endotracheal intubation and mechanical ventilation during surgery.

The methods of the present invention generally require the step of producing a mixed electrical signal comprising the combination of a first electrical signal and a second electrical signal, the first electrical signal being representative of the sounds emanating from a first region of the patients body and the second electrical signal being representative of the sounds emanating from a second region of the patients body, said first and second electrical signals having been electronically amplified prior to being mixed. The methods further generally require the steps of converting the mixed electrical signal into a single display signal, preferably an auditory signal, and monitoring the display signal. According to a preferred practice of the present invention, the monitoring step comprises monitoring said display signal while reducing the contribution of said first electrical signal in said mixed signal to a value substantially less than the contribution of said second signal in said mixed signal.

Apparatus of the present invention comprise at least two electronic sound sensing devices for detecting sounds of biological origin and producing an electrical signal representative of said detected sounds. Means for independently and adjustably amplifying the electrical signal produced by each of said sensing devices is also provided. The apparatus further includes means for mixing said amplified electrical signals to produce a mixed electrical signal. The output of the mixing means is connected to a signal transducer for converting said mixed electrical signal into a display signal.

BRIEF DESCRIPTION OF THE DRAWING

FIG. 1 is a schematic representation of one embodiment of the apparatus of the present invention.

FIG. 2 is a schematic representation of another embodiment of the apparatus of the present invention.

DESCRIPTION OF PREFERRED EMBODIMENTS

The methods of the present invention require the step of producing a mixed electrical signal comprising a combination of a first electrical signal and a second electrical signal, said first and second electrical signals being representative of sounds emanating from first and second regions of the patients body, respectively. As the terms are used herein, sounds emanating from a given region of a patients body refers to sounds produced predominantly from a particular organ or a distinct segment of an organ. According to a preferred aspect of the present invention, the first and second electrical signals are representative of sounds emanating from distinct segments of the lung, and more particularly from the right and left lung fields, respectively. According to other preferred embodiments, the producing step comprises producing a mixed electrical signal including a third electrical signal, said third signal being derived from a third region of the patients body, preferably from the cardiac region of the body.

The step of producing a mixed electrical signal according to the present invention preferably comprises producing said first electrical signal by placing a sound sensing device, such as disclosed hereinafter, in operative association with the appropriate region of the body. For example, in certain preferred embodiments of the present invention, a first sound sensing device is placed in operative association with the left chest wall of the patient to produce a first electrical signal representative of the sounds emanating from the left lung, and a second sound sensing device is placed in operative association with the right chest wall of the patient to produce an electrical signal representative of the sounds emanating from the right lung. Such a placement of sound sensing devices is especially preferred for the monitoring of bilateral ventilation and for the detection of ventilation problems that occur during surgery. Details concerning exact anatomical placement of such sound sensing devices in order to detect the preferred heart and lung sounds of the present invention are well known to those skilled in the art and therefore are not generally discussed in the present specification. It is generally preferred that, when conducted in the surgical environment, the methods of the present invention include the step of removably attaching the sensing devices to the appropriate portions of the patients body by, for example, taping the transducer to the body with double sided adhesive tape, as is well known in the art.

The sound sensing devices of the present invention preferably include or are connected to a signal amplification means for permitting manual adjustment of the amplification of said first, second and third signals independently of one another. Such a means is described more fully hereinafter.

The methods of the present invention further require converting the mixed electrical signal into a display signal. As the term is used herein, display signal refers to any signal that is readily detectable by the human senses, such as a visual signal or an auditory signal. As the term is used herein, auditory signal refers to any manifestation readily detectable by the sense of hearing. The use of display signals comprising auditory signals is preferred according to the present invention. Applicants have found that an auditory signal is the most readily adaptable for continuous monitoring and does not interfere with the other monitoring requirements of the anesthesiologist during surgery. Moreover, applicants have found that it is preferable for the auditory signals produced by the present invention to closely resemble the sounds detected by the sensing device. That is, it is preferred that the electrical signals produced by said sensing device be substantially unfiltered and unaltered electrical signals. In this way, the anesthesiologist monitors sounds that are familiar and readily diagnosable. As the term is used herein, a substantially unfiltered and unaltered electrical signal means a signal that has not been modified to such an extent that significant alteration of the basic sound detected by the sound sensing device occurs. Modification of the signal for the purpose of boosting its strength or eliminating background noise/hiss is not considered a sufficient alteration.

The use of electrical signals and their subsequent conversion to display signals according to the present invention is an important aspect of the present invention for several reasons. For example, the use of electrical signals to carry the detected information tends to preserve sound quality with little or no attenuation over relatively long distances using simple and inexpensive equipment. Moreover, the production of an auditory signal according to the present invention allows the attending physician or clinician to simultaneously monitor the sounds detected by each of the sound detecting devices. The production of an auditory signal according to the present invention also permits the use of a single or monaural ear piece to monitor all of the pertinent sounds. As described in D. Nelson, "A Monaural Stethoscope for Anesthesiologists", *Anesthesia and Analgesia*, Vol 51, No.2 (1972), the use of a monaural ear piece is especially desirable for an anesthesiologist in a surgical setting. Many of the prior art devices discussed above preclude the use of such a device and the advantages attendant thereto. For example, the devices disclosed in Waring et al, Wooten et al and Huang et al all appear to preclude the use of a single ear piece since the sounds detected by the separate sources all appear to be produced separately.

The step of monitoring the display signal generally comprises monitoring said display signal while reducing the contribution of said first electrical signal in said mixed signal to a value substantially less than the contribution of said second signal in said mixed signal. According to a preferred aspect of the present invention, said monitoring step comprises initially monitoring said display signal while reducing the amplification of said first electrical signal to a value substantially less than the amplification of said second electrical signal, the initial amplifications of said first and second electrical signals preferably being substantially equivalent. As will be appreciated by those skilled in the art, the actual values of the signal amplifications according to the present invention will depend upon a great many factors, including the sensitivity of the physicians ear, the sensitivity of the sound sensing transducer, and the distance over which transmission occurs. Accordingly, all such amplifications are within the scope of the present invention. Moreover, as used with respect to the electrical signals described herein, the term "substantially less" generally refers to a sufficient difference in contribution or amplification to cause the display signal to be predominated by one or more of the other sounds being detected. Thus, for each of the monitoring steps described above, it is only the relative amplification of the various signals that is considered to be of importance. According to certain embodiments, said initial monitoring step comprises reducing said first signal to a substantially zero amplification so as to eliminate said first signal from the mixed signal.

According to a preferred aspect of the present invention, the monitoring step further comprises subsequently monitoring said display signal while reducing the amplification of said second electrical signal, preferably from an amplification corresponding to about the amplification of said first electrical signal, to an amplification substantially less than the amplification of said first electrical signal. The monitoring step preferably further comprises a monitoring step intermediate said initial and said subsequent monitoring steps, wherein said intermediate step comprises monitoring said display signal while increasing said first electrical signal from an amplification substantially less than the amplification of said second electrical signal to an amplification substantially equal to about the amplification of said second electrical signal.

The monitoring steps described above are important features of the methods of the present invention, especially when the methods are applied to the detection of patient ventilation problems such as right mainstem intubation. In such embodiments, the first and second sound transducers are placed in operative association with the right and left chest wall of the patient, respectively. That is, the first transducer is placed so as to detect sounds emanating from the left lung and the second transducer is placed so as to detect sounds emanating from the right lung. The preferred methods require that at an initial point during the monitoring step the respective signals have substantially equal values. In this way, the attending physician hears both the left and right lung sounds simultaneously and makes a comparison of sound quality at the same amplification level. By requiring the initial monitoring step described above, the attending physician monitors the sound emanating from one side of the lung as the sound from the other side of the lung is reduced. The physician thus converts to a diagnostic mode in which he monitors predominantly only one of the two lung sounds. This is an important aspect of the present invention because it assures that the sound emanating from alternate sides of the chest are quickly and conveniently monitored by a simple adjustment of the amplification of the appropriate electrical signal. The need to engage in actual physical movement of the sound detecting device during surgery, as would be required by prior art auscultation techniques, is eliminated. In addition, applicants have found that the methods of the present invention are more reliable than many traditional prior art techniques for detecting patient ventilation problems, as illustrated in the Example described hereinafter.

Apparatus of the present invention are generally adaptable for use according to the methods of the present invention. As shown schematically in FIG. 1, the present apparatus require at least two, and preferably three, sound sensing devices 10A, 10B and 10C for detecting sounds 11A, 11B and 11C of biological origin and for producing electrical signals 12A, 12B and 12C representative of the detected sounds. According to a preferred embodiment of the present invention, the sound sensing device comprises a standard Wenger type precordial stethoscope bell, for example as shown at page 25 of the medical equipment catalogue attached hereto and incorporated herein by reference. The standard bell is preferably modified by locating a miniature condenser microphone within the sound chamber of the bell. The microphone may be maintained within the chamber by any known means, such as by fitting the stem of the microphone securely in a bore in the sidewall of the bell. Such a configuration has the advantage of providing easy access to the electrical connections that extend from the stem of most standard miniature microphones. It is also preferred that the microphone be electrically insulated from the bell, for example by surrounding the microphone stem with an insulating tube in the area of bell side wall, so as to avoid imparting an electrical shock to the patient. Applicants have found that a preferred sensing device comprises a Wenger Weighted Bell No. 00-390A having a condenser microphone located in the sound chamber thereof. For the purposes of consistency and simplicity, it is preferred that the sound sensing devices 10A, 11B and 10C are substantially identical sound sensing devices.

As shown in the schematic diagram of FIG. 1 the electronic signals, represented schematically as 12A, 12B and 12C, are directed to means for independently and adjustably amplifying those signals. In the embodiment of FIG. 1, the amplifying means comprises three variable gain amplifiers 13A, 13B and 13C, each electrically connected to a separate one of said sensing devices. According to a preferred embodiment, each of the amplifying means comprises a two-stage variable gain operational amplifier substantially as shown in FIG. 2. In the embodiment of FIG. 2, the variability of amplification is provided by a variable resistor connected between the input signal and the first stage of the amplifier.

The output signals 14A, 14B and 14C from amplifiers 13A, 13B and 13C are directed to means 15 for combining the three electrical signals to produce a mixed electrical signal 16. The mixed electrical signal 16 of the present invention thus includes amplified signals produced by the sensing devices 10A, 10B and 10C. Many means are well known in the art for mixing a plurality of electrical signals and all such means are within the scope of the present invention. For a detailed discussion of electronic mixers and the design thereof, see "Frequency Converters and Detectors" in the Electronics Engineers, Handbook, 2nd Edition, pages 14–56 to 14–70, incorporated herein by reference. One simple and effective mixing means comprises each of said amplifiers 13A, 13B and 13C having an output lead and means for assuring that the output lead of each amplifier is in electrical contact with the output lead of the other amplifiers. The output 16 from the mixing means 15 is connected to a an attenuator 17 for controlling the amplification of the mixed electrical signal.

The output 18 from the attenuator 17 is directed to a transducer 19 for converting the mixed electrical signal 18 to a display signal 20. Many such transducers are well known and readily available, and all such transducers are within the scope of the present invention. In certain embodiments, transducer 17 comprises a monaural or biaural electronic ear piece of standard design. In another embodiment, transducer 17 comprises an infrared, or preferably frequency modulated (FM), transmitter adapted to transmit infrared or FM signals based upon the mixed electrical signal 18 and an infrared, of FM receiver adapted to receive the infrared, or FM, signal and convert it to a display signal. A transducer of this general type is disclosed in the article entitled "Group Teaching of Auscultation-Uses of New Wireless Stethoscope-Type Headphone", *The American Journal of Cardiology*, deLeon et al, (1978).

EXAMPLE

Fifteen ASA physical status I or II patients were studied under surgical conditions using a variety of monitoring techniques and devices. In particular, the thoracic sounds of each patient were monitored with a heavy bell acoustic precordial stethoscope placed over the left anterior chest. An esophageal stethoscope was also placed in each patient to detect maximum loudness of breath sounds. An electronic stethoscope substantially as shown and described herein (hereinafter referred to as "the electronic stethoscope") was also used to monitor each patient. The first and second sensing devices of the electronic stethoscope were placed and maintained over similar bronchopulmonary segments of the left and right axilla of each patient. The third sensing device was placed and maintained over the midline of the anterior chest wall. For each patient, induction of anesthesia was standardized and the trachea orally intubated.

Using fiberoptic bronchoscopy, the endotracheal tube was manipulated into the distal trachea of six patients (hereinafter "the endotracheal group") and into the right mainstem bronchus of the remaining nine patients (hereinafter the "endobronchial group"). Ventilation was controlled using 10 cc/kg tidal volume and a rate of 12 breaths per minute. Nitrous oxide, oxygen and isoflurane were used for maintenance of anesthesia.

For each patient in the study, a first observer, blinded to the final position of the endotracheal tube, listened in serial fashion to the acoustic stethoscope, the esophageal stethoscope, and the auditory signal produced by the embodiment of the present invention shown in FIG. 2. In particular, the observer first monitored the auditory signal with the amplification of each electrical signal being substantially the same, then conducted an initial monitoring step in which the amplification of the second and third signals were reduced to substantially zero. Such a monitoring step was repeated until the observer had monitored each channel independently.

For each patient in the study, a second blinded observer diagnosed tube location using the following techniques: bilateral auscultation with a standard stethoscope; sternal notch palpation for the presence of an endotracheal tube cuff; and observed centimeter tube markings at the incisors.

The test was conducted over a five minute period for each patient. At the end of the 5 minutes, the tube was withdrawn until the cuff could be palpated within the sternal notch.

Biographical and physiologic data were analyzed by paired and unpaired t-tests. Auscultatory methods were compared using the McNemar Test with Bonferroni correction. A p value less than about 0.05 was considered statistically significant.

Based upon the tests described above, the apparatus and methods of the present invention were found to significantly improve the on-line diagnosis of the right mainstem intubation when compared to an esophageal stethoscope. Trends also suggest that the present invention provides an improvement over the standard precordial stethoscope, although statistical significance was not achieved. An incorrect diagnosis was never made using the methods and apparatus of the present invention.

Bilateral auscultation with the standard stethoscope and observation for equal chest wall excursion were found to be highly accurate when diagnosing a right mainstem intubation. However, as mentioned before, such techniques are generally not practical in a surgical setting. Moreover, several endotracheal intubations were misdiagnosed as being endobronchial when bilateral auscultatation with a standard stethoscope was used. The diagnosis of right mainstem intubation using $FIO_2$ concentration, lowest hemoglobin saturation, and average end-tidal $CO_2$ concentration were not found to be significantly different between the two groups. The results of this test are summarized in Tables 1 and 2 below.

TABLE 1

| ENDOTRACHEAL GROUP | |
|---|---|
| Instrument Readings | Average Value |
| $FIO_2$, % $O_2$ concentration | 0.44 ± 0.14 |
| $SaO_2$ - Lowest, % saturation | 99.3 ± 1.0 |
| Peak airway pressure @ 5 min, cm of $H_2O$ | 20.8 ± 4.8 |
| End-Tidal $CO_2$ @ 5 min, mm of Hg | 32.5 ± 4.0 |
| Tube Marking, cm | 22.5 ± 4.13 |
| Diagnostic Technique | % Correct Diagnosis |
| Electronic Stethoscope | 100% |
| Acoustic Stethoscope | 83% |
| Esophageal Stethoscope | 100% |
| Bilateral Auscultation (using Standard Stethoscope) | 83% |
| Cuff Palpation | 50% |
| Chest Wall Movement | 83% |

TABLE 2

| ENDOBRONCHIAL GROUP | |
|---|---|
| Instrument Readings | Average Value |
| $FIO_2$, % $O_2$ concentration | 0.46 ± 0.18 |
| $SaO_2$ - Lowest, % saturation | 98.8 ± 1.7 |
| Peak airway pressure @ 5 min., cm of $H_2O$ | 24.7 ± 4.4 |
| End-Tidal $CO_2$ @ 5 min, mm of Hg | 29.7 ± 4.0 |
| Tube Marking (cm) | 28.1 ± 0.78 |
| Diagnostic Technique | % Correct Diagnosis |
| Electronic Stethoscope | 100% |
| Acoustic Stethoscope | 78% |
| Esophogeal Stethoscope | 22% |
| Bilateral Auscultation (using Standard Stethoscope) | 100% |
| Cuff Palpation | 0% |
| Chest Wall Movement | 100% |

What we claim is:

1. An apparatus for monitoring the heart and breath sounds of a patient comprising:
    (a) a first sound sensing device, comprising means for detecting first sounds of biological origin and for producing a first electrical signal representative of said first detected sounds;
    (b) a second sound sensing device comprising means for detecting second sounds of biological origin and for producing a second electrical signal representative of said second detected sounds;
    (c) means for independently and adjustably amplifying said first electrical signal;
    (d) means for independently and adjustably amplifying said second electrical signal
    (e) means for mixing said amplified signals to produce a mixed electrical signal comprising said first and said second electrical signals; and
    (f) means for converting said mixed electrical signal into a display signal representative of said first and second sounds.

2. The apparatus of claim 1 wherein at least one of said sound sensing devices comprises a weighted Wegner type bell defining a sound chamber and a microphone located within or adjacent to said sound chamber.

3. The apparatus of claim 2 wherein said bell is a Wegner Weighted Bell No. 00-390A.

4. The apparatus of claim 2 wherein said microphone is a miniature condenser microphone.

5. The apparatus of claim 1 wherein each of said amplifying means comprises a variable gain amplifier connected to one of said sound sensing devices.

6. A method of detecting the presence or absence of bilateral ventilation in a patient undergoing a surgical operation comprising:
 (a) placing a first sound sensing device in operative association with the left chest wall of said patient to produce a first electrical signal representative of the sounds emanating from the left lung;
 (b) placing a second sound sensing device in operative association with the right chest wall of said patient to produce a second electrical signal representative of the sounds emanating from the right lung;
 (c) mixing said first and second electrical signal to produce a mixed electrical signal comprising said first and second electrical signals, said first and second signals having been amplified prior to mixing;
 (d) converting the mixed electrical signal to an auditory signal comprising a combination of said first and second sounds; and
 (e) monitoring said auditory signal.

7. The method of claim 6 wherein said monitoring step comprises initially monitoring said auditory signal while reducing the amplification of said first electrical signal to a value substantially less than the amplification of said second electrical signal.

8. The method of claim 7 wherein the amplification of said first electrical signal is substantially equal to the amplification of said second signal at the start of said initial monitoring step.

9. The method of claim 8 wherein said monitoring step further comprises a subsequent monitoring step after said initial monitoring step, said subsequent monitoring step comprising monitoring said auditory signal while reducing the amplification of said second electrical signal to a value substantially less than the amplification of said first electrical signal.

10. The method of claim 9 wherein the initial amplification of said first and second electrical signals are substantially equivalent at the start of said subsequent monitoring step.

11. The method of claim 9 wherein said monitoring step comprises an intermediate monitoring step between said initial and said subsequent monitoring steps, said intermediate step comprising monitoring said auditory signal while increasing said first electrical signal from an amplification substantially less than the amplification of said second electrical signal to an amplification substantially equal to about the amplification of said second electrical signal.

12. A method of monitoring sounds emanating from the body of a patient comprising:
 (a) producing a mixed electrical signal comprising a combination of a first electrical signal and a second electrical signal, said first electrical signal being representative of sounds emanating from a first region of the patient's body and said second electrical signal being representative of sounds emanating from a second region of the patient's body;
 (b) converting the mixed electrical signal to a display signal; and
 (c) monitoring said display signal while reducing the contribution of said first signal in said mixed signal to a value substantially less than the contribution of said second signal in said mixed signal.

13. The method of claim 12 wherein said mixed electrical signal comprises a combination of said first electrical signal, said second electrical signal and a third electrical signal, said third electrical signal being representative of sounds emanating from a third region of the patient's body.

14. The method of claim 12 wherein said producing step comprises placing a first sound sensing device in operative association with said first region of the patient's body and placing a second sound sensing device in operative association with said second region of the patient's body.

15. The method of claim 12 wherein said display signal comprises an auditory signal.

16. The method of claim 15 wherein said first and second electrical signals are independently amplified prior to being mixed.

17. The method of claim 16 wherein said step of monitoring comprises monitoring said auditory signal while reducing the amplification of said first signal to a value substantially less than the amplification of said second signal.

18. The method of claim 17 wherein said monitoring step comprises monitoring said auditory signal while reducing the amplification of said first signal sufficiently to eliminate said first signal from said mixed signal.

* * * * *